(12) United States Patent
Brandvold et al.

(10) Patent No.: US 7,288,684 B1
(45) Date of Patent: Oct. 30, 2007

(54) PROCESS FOR THE DIRECT PRODUCTION OF METHANOL FROM METHANE

(75) Inventors: Timothy A. Brandvold, Arlington Heights, IL (US); Joseph A. Kocal, Glenview, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 11/560,960

(22) Filed: Nov. 17, 2006

Related U.S. Application Data

(60) Provisional application No. 60/753,205, filed on Dec. 22, 2005.

(51) Int. Cl.
C07C 27/12 (2006.01)

(52) U.S. Cl. .................................... 568/910.5

(58) Field of Classification Search ............. 568/910.5, 568/910
See application file for complete search history.

(56) References Cited

U.S. PATENT DOCUMENTS

| | | | |
|---|---|---|---|
| 4,601,907 A | 7/1986 | Knebl | |
| 4,911,937 A | 3/1990 | Crosello et al. | |
| 4,971,806 A | 11/1990 | Cherukuri et al. | |
| 5,002,791 A | 3/1991 | Knebl | |
| 5,270,061 A | 12/1993 | Reed et al. | |
| 5,362,508 A | 11/1994 | Wheeler et al. | |
| 5,437,879 A | 8/1995 | Kabse et al. | |
| 5,578,336 A | 11/1996 | Monte | |
| 5,585,515 A | 12/1996 | Camaioni et al. | 560/227 |
| 6,183,799 B1 | 2/2001 | Wu et al. | |
| 6,200,603 B1 | 3/2001 | Rowe et al. | |
| 6,280,780 B1 | 8/2001 | Degady et al. | |
| 6,350,483 B1 | 2/2002 | Ahad et al. | |
| 6,358,547 B1 | 3/2002 | DuPont | |
| 6,558,727 B2 | 5/2003 | Degady et al. | |
| 6,562,382 B1 | 5/2003 | Corriveau et al. | |
| 6,592,928 B2 | 7/2003 | Makela et al. | |
| 6,616,963 B1 | 9/2003 | Zerby et al. | |
| 6,623,266 B2 | 9/2003 | Jani et al. | |
| 6,623,783 B1 | 9/2003 | Wong et al. | |
| 6,805,890 B2 | 10/2004 | Wu et al. | |
| 2003/0068422 A1 | 4/2003 | Rivier | |
| 2004/0037924 A1 | 2/2004 | Jani et al. | |
| 2004/0037925 A1 | 2/2004 | Jani et al. | |
| 2005/0084603 A1 | 4/2005 | Kaiser et al. | |
| 2005/0152969 A1 | 7/2005 | Chiprich | |
| 2006/0045934 A1 | 3/2006 | Kabse et al. | |
| 2006/0051456 A1 | 3/2006 | Kabse et al. | |
| 2006/0110442 A1 | 5/2006 | Wonschik et al. | |
| 2006/0110493 A1 | 5/2006 | Schnieber at al. | |

FOREIGN PATENT DOCUMENTS

| | | |
|---|---|---|
| DE | 1 510 996 | 5/1978 |
| GB | 2 283 899 | 5/1995 |
| JP | 49-125562 | 12/1974 |
| JP | 50-089585 | 7/1975 |
| JP | 51-038447 | 3/1976 |
| JP | 51-148050 | 12/1976 |
| JP | 60-070036 | 4/1985 |
| JP | 2-039875 | 2/1990 |
| JP | 7-246053 | 9/1995 |
| JP | 9-051789 | 2/1997 |
| JP | 10-337149 | 12/1998 |
| JP | 3062496 | 7/1999 |
| JP | 2001-231531 | 8/2001 |
| JP | 2004-517628 | 6/2004 |
| JP | 38-23087 | 9/2006 |
| WO | WO98/54977 | 12/1998 |
| WO | WO 02/056698 | 7/2002 |
| WO | 2005/002352 | 1/2005 |
| WO | 2005/048728 | 6/2005 |
| WO | 2005/063037 | 7/2005 |
| WO | 2005/077521 | 8/2005 |
| WO | 2006/026298 | 3/2006 |

OTHER PUBLICATIONS

Sen et al. in *New J. Chem*, 1989, 13, 755-760.
E.D. Park et al. in *Catalysis Communications*, vol. 2 (2001), 187-190.
L.C. Kao et al. in *J.Am.Chem.Soc.*, 113 (1991), 700-701.
U.S. Appl. No. 10/418,020, filed Apr. 17, 2003.
U.S. Appl. No. 11/027,903, filed Dec. 29, 2004.
PCT/US04/043872, Dec. 29, 2004.
2-Stage Liquid Mints "Hershey Chocolate USA" "Ice Breakers Center Ice", Internet Google search online, Record ID 10245696, Mintel Group (2 pp.), 1998.
Baker Perkins, Innovative candy mould design, http://www.apvbaker.com/news/154.php, News What's New—Innovative candy mould design, Oct. 27, 2006 (2 pp.).
Baker Perkins, Welcome to Baker Perkins' Confectionery Sector, http://www.apvbaker.com/confectionery, Business Sectors—Confectionery, Oct. 27, 2006 (1 pg.).
APV Baker Quality Confectionery, Apr. 2005, (12 pp.).
Confectionery Technologies, BOSCH, Mar. 2002 (22 pp.).

*Primary Examiner*—Elvis O. Price
(74) *Attorney, Agent, or Firm*—Frank S. Molinaro

(57) ABSTRACT

A process for the production of methanol from methane has been developed. The process involves reacting methane with an oxidant such as oxygen or a peroxide in the presence of a catalyst and a solvent in a reaction zone to produce an effluent stream comprising a methanol product. The effluent stream is next separated into a gaseous stream comprising unreacted methane and carbon dioxide and a liquid stream comprising the methanol product and solvent. Next the gaseous stream is further separated to provide a methane stream which is recycled to the reaction zone. Finally, a methanol stream is isolated and a solvent stream is recycled to the reaction zone.

10 Claims, 1 Drawing Sheet

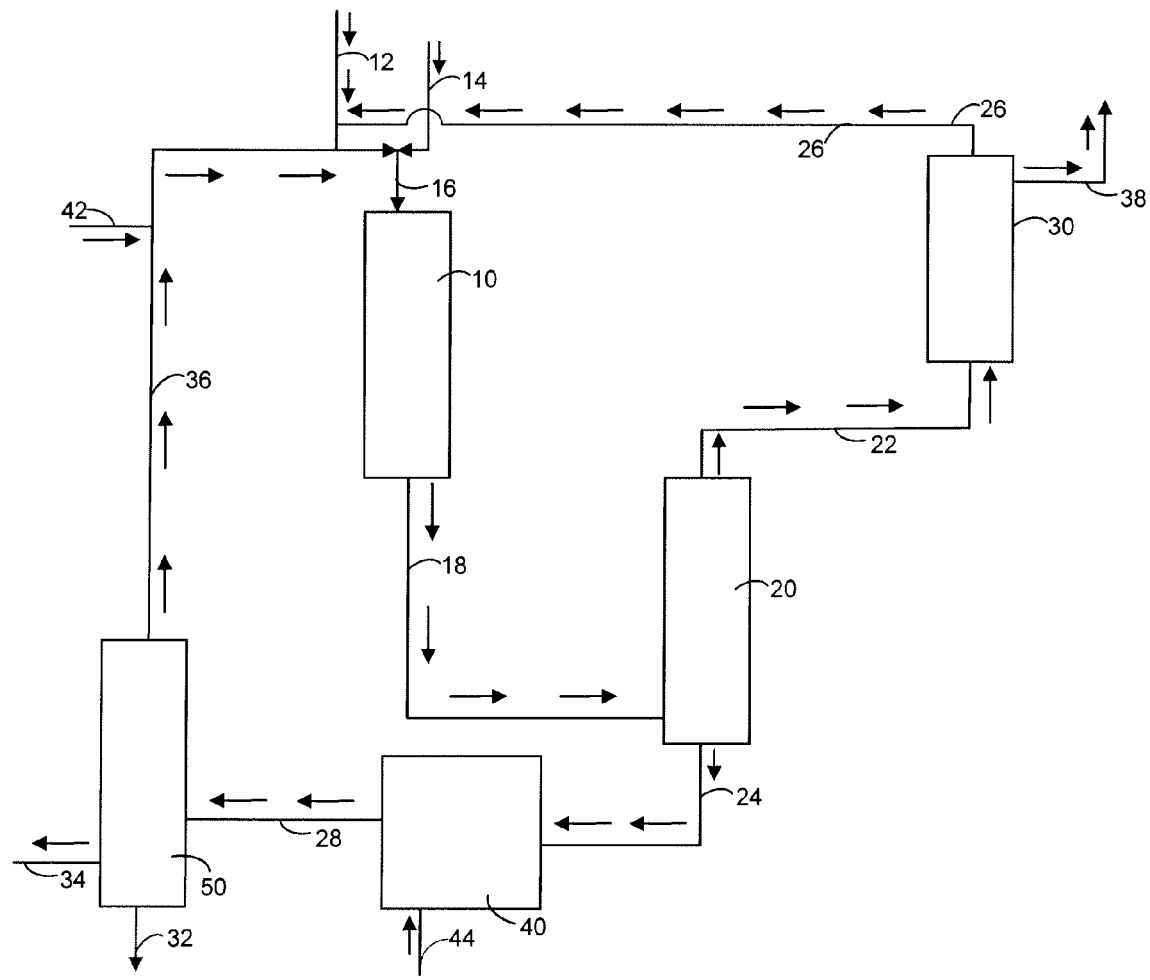
Figure

PROCESS FOR THE DIRECT PRODUCTION OF METHANOL FROM METHANE

CROSS REFERENCE TO RELATED APPLICATION

This application claims priority from Provisional Application Ser. No. 60/753,205 filed Dec. 22, 2005, the contents of which are hereby incorporated by reference in its entirety.

FIELD OF THE INVENTION

The invention relates to a process for converting methane to methanol. The process involves either co-feeding or alternately feeding methane and an oxidant to a reactor containing a catalyst at oxidation conditions to convert the methane to methanol. The effluent from this oxidation reactor is separated into a gaseous stream comprising unreacted methane and a bottom stream comprising methanol or a methanol adduct. The gaseous stream is further separated to provide a methane stream which is recycled to the reactor, while the bottom stream is separated into a methanol stream and a solvent stream which is also recycled to the reactor.

BACKGROUND OF THE INVENTION

Today, both chemical and energy industries rely on petroleum as the principal source of carbon and energy. Methane is underutilized as a chemical feedstock, despite being the primary constituent of natural gas, an abundant carbon resource. Factors limiting its use include the remote locations of known reserves, its relatively high transportation costs and its thermodynamic and kinetic stability. Methane's main industrial use is the production of synthesis gas or syngas via steam reforming at high temperatures and pressures. Syngas in turn can be converted to methanol also at elevated temperatures and pressures. The production of methanol is important because methanol can be used to produce important chemicals such as olefins. The above two step process for the production of methanol is expensive and energy intensive with corresponding environmental impacts.

Selective oxidation of methane has been studied for over 30 years by individual, academic and government researchers with no commercial success. The key challenges to a commercial direct methane oxidation process are the inertness of methane relative to intermediates and oxygenate products and designing a catalytic process for direct gas phase reaction with high conversion and selectivity. For example, Sen et al. in *New J. Chem*, 1989, 13, 755-760 disclose the use of Pd $(O_2C\ Me)_2$ in trifluoroacetic acid for the oxidation of methane to $CF_3CO_2Me$. The reaction is carried out for 4 days at a pressure of 5516-6895 kPa (800-1000 psi). E. D. Park et al. in *Catalysis Communications*, Vol. 2 (2001), 187-190, disclose a Pd/C plus Cu $(CH_3COO)_2$ catalyst system for the selective oxidation of methane using $H_2/O_2$. L. C. Kao et al. in *J. Am. Chem. Soc.*, 113 (1991), 700-701 disclose the use of palladium compounds such as Pd $(O_2CC_2H_5)_2$ to oxidize methane to methanol in the presence of $H_2O_2$ and using trifluoroacetic acid as the solvent. U.S. Pat. No. 5,585,515 discloses the use of catalysts such as Cu(I) ions in trifluoroacetic acid to oxidize methane to methanol.

Applicants have developed a process which efficiently produces a methanol stream from methane. Generally, the process comprises reacting methane and an oxidant in the presence of a catalyst at oxidation conditions. The resultant product mixture is next processed to give a purified methanol stream and recycle methane and solvent streams.

SUMMARY OF THE INVENTION

One embodiment of the invention is a process for converting methane to methanol comprising:
  a) flowing a methane and an oxidant stream to a methane oxidation reactor and contacting the methane and oxidant with a catalyst and a solvent at oxidation conditions to provide an effluent stream comprising methanol or a methanol adduct;
  b) flowing the effluent stream to a separation zone operated at conditions to provide an overhead gaseous stream comprising methane and carbon dioxide and a bottom stream comprising methanol or a methanol adduct, solvent and byproducts;
  c) flowing the bottom stream to a second separation zone operated at conditions to provide a purified product stream comprising methanol, and a solvent stream which is recycled to the oxidation reactor; and
  d) flowing the overhead gaseous stream to a third separation zone operated at conditions to provide a methane stream which is recycled back to the oxidation reactor and a waste stream comprising carbon dioxide.

This and other objects and embodiments will become clearer after a detailed description of the invention.

BRIEF DESCRIPTION OF THE DRAWING

The FIGURE is a flow diagram showing one embodiment of the invention.

DETAILED DESCRIPTION OF THE INVENTION

The present invention relates to the selective oxidation of methane to methanol using a catalyst. The methane or feedstream can either be a pure methane stream or can be diluted with an inert gas such as nitrogen, helium, neon, argon, etc. Another element of the invention is an oxidant which will react with the methane. The oxidant can be oxygen, hydrogen peroxide or an organic hydroperoxide. Non limiting examples of organic hydroperoxides include tert-butyl hydroperoxide, cumene hydroperoxide, etc. It is also within the scope of the invention that a blend of hydrocarbons such as gasoline, straight run diesel, light cycle oil, vacuum gas oil, fuel oil and crude oil can be oxidized to give a mixture of organic hydroperoxides. One process for producing these hydroperoxides is disclosed in U.S. Pat. No. 7,038,090 B1 which is incorporated by reference in its entirety.

The oxidant stream and methane are now flowed into an oxidation reactor or oxidation zone where they are reacted in the presence of a catalyst to produce methanol. The oxidant and methane streams can either be introduced into the oxidation zone in an alternate arrangement or they can be combined into one stream and than flowed into the oxidation zone. The oxidation zone will contain a catalyst for promoting the oxidation of methane to methanol and a solvent. The catalyst can either be a heterogeneous catalyst or a catalytic metal compound which is dissolved in the solvent, i.e. a homogeneous catalyst.

The metal compounds which can be used have an empirical formula of $M_xX_m$ where M is selected from the group consisting of palladium, copper, manganese, mercury, silver, cobalt, vanadium, platinum, lead, gold, niobium, chromium, molybdenum, tungsten, cerium and mixtures thereof, X is an anion; examples of which include but are not limited to acetate, trifluoroacetate, sulfate, carbonate, halide, nitrate, perchlorate, propionate, pentafluoropropionate, acetylacetonate, and hexafluoroacetylacetonate, "m" is the oxidation state of M, and "x" is the anion valence of X. The compounds described above are readily available from commercial suppliers, can be prepared by known methods or in certain cases can be prepared in situ by dissolving the corresponding metal oxide in the reaction solvent. For example, copper oxide can be dissolved in trifluoroacetic acid to provide copper trifluoroacetate.

Another component of the invention is a solvent in which the metal compounds described above are soluble. Non limiting examples of solvents are trifluoroacetic acid, trifluoroacetic anhydride, pentafluoropropionic acid, acetic acid, supercritical carbon dioxide and mixtures thereof with trifluoroacetic acid being preferred. The amount of compound which is added to the solvent can vary widely, but is usually from about 0.01 weight % to about 2 weight % of M as the metal.

Non limiting examples of heterogeneous catalysts include the oxides of metals such as manganese, cobalt, palladium, molybdenum, chromium, vanadium and copper, and composite materials where one or more of these oxides is supported on silica, alumina, zirconia, magnesia, carbon, silicon carbide and other supports known in the art. The catalyst may also include additional non-catalytically active components which act as catalyst modifiers including but not limited to lithium, sodium, potassium, tin, germanium, sulfur, boron, chlorine. The heterogeneous catalyst can be present as a fixed bed or can be used in a riser/regenerator reactor. In the case of a homogeneous catalyst, the reactor can be a continuous autoclave or the process can be carried out in a batch mode. Regardless of what type of reactor is employed, the oxidation conditions include a pressure of about 103 kPa (15 psi) to about 6,895 kPa (1,000 psi) and preferably from about 4,137 kPa (600 psi) to about 6,895 kPa (1,000 psi). These pressures are sufficient to ensure that the methane is dissolved in the liquid phase and the reaction is a liquid phase reaction. Of course if the oxidant is oxygen, it will be in the gas phase in the reactor. The reaction temperature varies from about 25° C. to about 250° C. and preferably from about 60° C. to about 100° C. The contact time can vary considerably, but is usually from about 30 minutes to about 24 hours. The product mixture will contain either methanol or a methyl ester formed from the methane and an adduct from the solvent. Additional components of the product mixture will include unreacted methane (the reaction is carried out with the oxidant as the limiting reagent), $CO_2$ (which results from the degradation of the solvent) and higher molecular weight alcohols which are byproducts from the organic hydroperoxide which may be used as the oxidant.

The product stream or effluent stream from the oxidation reactor or oxidation zone is now flowed to a separation zone which is operated at conditions to provide an overhead gaseous stream and a liquid bottom stream. The overhead stream will comprise methane and carbon dioxide while the liquid bottom stream will comprise methanol, solvent, water and byproducts. The separation conditions in this separation zone include a temperature of about 50° C. to about 200° C. and a pressure of about 103 kPa (15 psi) to about 6895 kPa (1000 psi).

The liquid bottom stream is now flowed to a second separation zone operated at conditions to provide a purified methanol product stream, a solvent stream and a byproduct greater than or equal to C2 alcohol stream. The second separation zone can utilize any method known in the art including distillation and adsorptive separation. For separation by distillation typical conditions include a temperature of 20-240° C., and a pressure of 103 kPa (15 psi) to about 1030 kPa (150 psi). However, if the liquid bottom stream contains methyl ester adducts, the stream must first be passed to a hydrolysis zone where the methyl ester is hydrolyzed to methanol and regenerate the solvent. Hydrolysis conditions include a temperature of about 20° C. to about 200° C. and a pressure of about 103 kPa (15 psi) to about 1030 kPa (150 psi). A co-solvent and/or catalyst, well-known in the art, may also be introduced to the reactor to facilitate hydrolysis. Once the methyl ester adduct is hydrolyzed, it is now flowed to the second separation zone and treated as described above. The solvent stream is now recycled to the oxidation reactor, but since there may have been degradation of the solvent, makeup solvent may be added to this stream prior to introducing it back into the oxidation reactor. The methane feedstream and the methane recycle stream (as described below) can also be added to the solvent stream which is than either directly flowed into the oxidation reactor or combined with the oxidant stream and than flowed into the oxidation reactor.

The overhead gaseous stream is now flowed to a third separation zone which is operated at conditions to provide a methane stream and a waste stream comprising carbon dioxide. The methane stream is recycled back to the oxidation reactor by flowing it into the recycle solvent stream.

Referring now to the FIGURE, methane or a methane/inert gas stream is introduced via line 12 which may be combined with recycle methane from line 26 and than in turn combined with the recycle solvent stream 36 flowed into line 16 and into reactor 10. The oxidant is flowed through line 14 into the valve connecting it with line 36 containing solvent and methane which in turn is flowed into line 16 and then into reactor 10. The valve joining lines 14 and 36 can be operated in such a way that both the methane solvent stream and oxidant stream are joined together or the methane solvent stream is first flowed into the reactor and then followed by the oxidant stream with the two streams being alternately fed into reactor 10. Reactor 10 contains either a heterogeneous catalyst present as a catalyst bed or a homogeneous catalyst compound dissolved in the solvent. If the catalyst is a homogeneous catalyst, reactor 10 is charged with the homogeneous catalyst and heated tip to operating temperature prior to flowing oxidant and methane into the reactor. Once the methane and oxidant are contacted for a sufficient time (as described above) in order to convert the methane to methanol, the effluent or product mixture is flowed out the reactor via line 18 and into reactor 20. Reactor 20 is a separation reactor or zone where the gaseous components of the effluent stream are separated from the liquid components. The gaseous components will comprise methane and carbon dioxide which form an overhead gaseous stream which is removed via line 22. This overhead gaseous stream is now flowed to a separation zone 30 which separates methane from the carbon dioxide. The methane is removed via line 26 and recycled to line 12 while the carbon dioxide is vented via line 38.

If the product from reactor 10 comprises a methyl ester, than the liquid bottom stream from reactor 20 is removed via line 24 and flowed into hydrolysis zone 40. Water is introduced, along with any catalysts and co-solvents, to the hydrolysis zone via line 44. In the hydrolysis zone, the liquid bottom stream is hydrolyzed to give methanol and regenerate the solvent. The effluent stream from the hydrolysis zone is now flowed via line 28 into separation zone 50. If methanol is the direct product from reactor 10, then the liquid bottom feed from reactor 20 is flowed directly via line 24 and 28 into separation zone 50. In separation zone 50, a purified methanol stream is separated and collected via line 32 while water, co-solvents from the hydrolysis zone, any higher molecular weight alcohols and other liquid by-products are removed via line 34 and the solvent is removed via line 36 and recycled back to reactor 10. Since some solvent degradation occurs and thus solvent is lost, additional solvent may need to be added via line 42.

While the invention has been described with what are presently considered the preferred embodiments, it is to be understood that the invention is not limited to the disclosed embodiments, but it is intended to cover various modifications and equivalent arrangements included within the scope of the appended claims.

What is claimed is:

1. A process for converting methane to methanol comprising:
   a) flowing a methane and an oxidant stream to a methane oxidation reactor and contacting the methane and oxidant with a catalyst and a solvent at oxidation conditions to provide an effluent stream comprising methanol or a methanol adduct;
   b) flowing the effluent stream to a separation zone operated at conditions to provide an overhead gaseous stream comprising methane and carbon dioxide and a bottom stream comprising methanol or a methanol adduct, solvent and byproducts;
   c) flowing the bottom stream to a second separation zone operated at conditions to provide a purified product stream comprising methanol, and a solvent stream which is recycled to the oxidation reactor; and
   d) flowing the overhead gaseous stream to a third separation zone operated at conditions to provide a methane stream which is recycled back to the oxidation reactor and a waste stream comprising carbon dioxide.

2. The process of claim 1 where the catalyst is a heterogeneous catalyst.

3. The process of claim 1 where the catalyst is a homogeneous catalyst.

4. The process of claim 1 where the solvent is selected from the group consisting of trifluoro-acetic acid, trifluoro-acetic anhydride, pentafluoro-proprionic acid, supercritical carbon dioxide and mixtures thereof.

5. The process of claim 1 where the oxidation conditions comprise a pressure of about 103 kPa (15 psi) to about 6,895 kPa (1,000 psi), a temperature of about 25° C. to about 250° C. and a contact time of about 30 minutes to about 30 hours.

6. The process of claim 1 where prior to step (c), the bottom stream is flowed to a hydrolysis zone operated at hydrolysis conditions thereby hydrolyzing at least a portion of the methanol adduct to methanol and regenerated solvent.

7. The process of claim 6 where the hydrolysis conditions comprise a temperature of about 20° C. to about 200° C. and a pressure of about 103 kPa to about 1030 kPa.

8. The process of claim 1 where the methane and oxidant streams are first mixed and then flowed to the oxidation reactor.

9. The process of claim 3 where the homogeneous catalyst comprises a compound dissolved in a solvent, the compound having an empirical formula of $M_xX_m$ where M is selected from the group consisting of palladium, copper, manganese, mercury, silver, cobalt, vanadium, platinum, lead, gold, niobium chromium, molybdenum, tungsten, cerium and mixtures thereof and X is an anion selected from the group consisting of acetate, trifluoroacetate, sulfate, carbonate, halide, nitrate, perchlorate, propionate, pentafluoropropionate, acetylacetonate, hexafluoroacetylacetonate, "m" is the oxidation state of M, and "x" is the anion valence of X.

10. The process of claim 2 where the catalyst is an oxide of a metal selected from the group consisting of manganese, cobalt, palladium, molybdenum, chromium, vanadium, copper and mixtures thereof.

\* \* \* \* \*